(12) United States Patent
Jun et al.

(10) Patent No.: US 6,252,118 B1
(45) Date of Patent: Jun. 26, 2001

(54) METHOD FOR THE PREPARATION OF KETONES

(75) Inventors: Chul Ho Jun, 103-1203, Doklipmoon Sambo APT., Youngchon-dong 100, Seodaemoon-ku, Seoul; Hyuk Lee, Seoul, both of (KR)

(73) Assignee: Chul Ho Jun, Seoul (KR)

( * ) Notice: Subject to any disclaimer, the term of this patent is extended or adjusted under 35 U.S.C. 154(b) by 0 days.

(21) Appl. No.: 09/579,423

(22) Filed: May 26, 2000

(51) Int. Cl.$^7$ .................................................... C07C 45/69
(52) U.S. Cl. ........................... 568/317; 568/349; 568/395
(58) Field of Search ............................... 568/317, 349, 568/395

(56) References Cited

PUBLICATIONS

Chelation–assisted intermolecular hydroacylation: Direct synthesis of ketone from aldehyde and 1–alkene. Jun et al., J. Org. Chem. 1997, 62, pp. 1200–1201.*

Activation of aldehyde C–H bonds to oxidative addition via formation of 3–methyl–2–aminopyridyl aldimines and related compounds: Rhodium based catalytic hydroacylation. SUGGS, J. Am. Chem. Soc., 1979, 101(2), p. 489.*

* cited by examiner

*Primary Examiner*—Johann Richter
*Assistant Examiner*—Brian J. Davis
(74) *Attorney, Agent, or Firm*—Harrison & Egbert

(57) ABSTRACT

A method for preparation of a new ketone from a preexisting ketone is very advantageous in terms of production cost and yield. A reactant mixture consisting of a ketone containing β-hydrogen relative to the aldehyde group and a vinyl olefin or internal olefin having an aliphatic or aromatic alkyl moiety is allowed to react at approximately 100–180° C. for at least 6 hours in the presence of a rhodium or iridium transition metal catalyst and a 2-aminopyridine derivative.

4 Claims, No Drawings

METHOD FOR THE PREPARATION OF KETONES

BACKGROUND OF THE INVENTION

1. Field of the Invention

The present invention relates, in general, to a method for the preparation of ketones and, more particularly, to a method for preparing novel ketones by use of a transition metal catalyst with the aid of a 2-aminopyridine derivative.

2. Description of the Related Art

Until recently, the introduction of carbonyl, one of the most important organic groups, into organic compounds has been in extensive study for preparing ketones. In one of the most typical methods, aldehyde is reacted to a nucleophilic organic metal compound, such as alkylmagnesium halide, to give bivalent alcohol which is then oxidized into ketone with the aid of various oxidizers. However, this method suffers from several disadvantages; it must pass through many reaction steps and it produces many unnecessary by-products during the reaction steps.

In an effort to avoid these problems, active research has been directed to hydroacylation techniques for preparing ketones directly from olefins and aldehyde. Of them, the preparation from aldehyde and olefins in the presence of a metal catalyst and 2-aminopyridine derivatives is actively studded for its simple feasibility under a mild conditions. According to this method, aldehyde is reacted with 2-aminopyridine to give aldimine which is then reacted with olefin through a metal catalyst, followed by hydrolysis to afford ketone. However, this method is disadvantageous in terms of high production cost and low production yield.

Meanwhile, no methods have been reported for the conversion of one ketone into a different one. In order to synthesize a new ketone from a preexisting one, the alkyl radical attached to the carbonyl group must be removed and substituted by a desired alkyl radical. There have not yet been developed methods for effectively cleaving the single bond between the carbon atom of a carbonyl group and the α-carbon atom.

BRIEF SUMMARY OF THE INVENTION

The thorough and intensive research on the synthesis of ketones, repeated by the present invention aiming to synthesize ketones with high yields and economical favors, resulted in the finding that transition metal catalysts can effectively cleave and link the single bond between the carbon of a carbonyl group and the α-carbon atom with the aid of a 2-aminopyridine derivative.

Therefore, it is an object of the present invention to overcome the above problems encountered in prior art and to provide a method for the preparation of ketone with high economical favor and yield.

In accordance with an embodiment of the present invention, there is provided a method for preparing a ketone, comprising the steps of: preparing a reactant mixture consisting of a ketone containing β-hydrogen relative to the aldehyde group and a vinyl olefin or internal olefin having an aliphatic or aromatic alkyl moiety as starting materials; and reacting the reactant mixture at approximately 100–180° C. for at least 6 hours in the presence of a rhodium or iridium transition metal catalyst and a 2-aminopyridine derivative.

In accordance with another embodiment of the present invention, there is provided a method for preparing a ketone, comprising the steps of: producing a ketimine through the condensation of a reactant ketone and 2-amino-3-pycoline; coordinating a transition metal catalyst to the pyridine radical of the ketimine to cleave a carbon-carbon bond of the reactant ketone and to subsequently remove a β-hydrogen to form an olefin; coordinating a substitute, different olefin to the metal of the catalyst to produce a different ketimine; and hydrolyzing the different ketimine with the water resulting from the condensation to recover the amine.

DETAILED DESCRIPTION OF THE INVENTION

The present invention is directed to the synthesis of new ketone compounds from preexisting ketone compounds in the presence of a transition metal catalyst and 2-aminopyridine derivatives as illustrated in the following reaction formula 1:

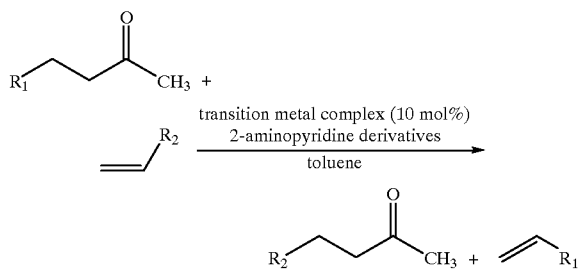

Useful as a starting material is a ketone which has a hydrogen at the β-position of the carbonyl group, such as benzyl acetone or 2-butanone. Where β-hydrogen exists on both sides of the carbonyl group, the alkyl radicals on both sides of the carbonyl group are cleaved and substituted by olefins to give dialkyl ketone.

In the present invention, olefins are used to make new ketone compounds. Almost all vinyl-containing olefins can be used for this purpose. Examples of transition metal catalysts suitable to promote this substitution include Wilkins catalysts such as (PPh$_3$)RhCl, rhodium monovalent catalysts such as [Rh(C$_8$H$_{14}$)$_2$]$_2$, and rhodium trivalent catalyst such as [RhCl$_3$.H$_2$O]. When rhodium trivalent catalysts or [Rh(C$_8$H$_{16}$)Cl]$_2$ is employed, a phosphine compound, such as triphenyl phosphine (PPh$_3$), is preferably added together.

In combination with the transition metal catalyst, a 2-aminopyridine derivative is used according to the present invention. Although a variety of 2-aminopyridine derivatives may be used, the most preferable is 2-amino-3-pycoline.

An organic solvent, if not indispensable for the synthesis, is helpful in reducing the time of the reaction. However, the reaction free of organic solvents enjoys advantages of minimizing the number of the reactors required, converting all the used materials, except for the catalysts, into the products so as to obtain high production yields, and reusing the used 2-aminopyridine derivative in its entirety.

In the presence of such catalysts, the reactants are reacted in the reaction mechanism shown in the following chemical reaction formula 2:

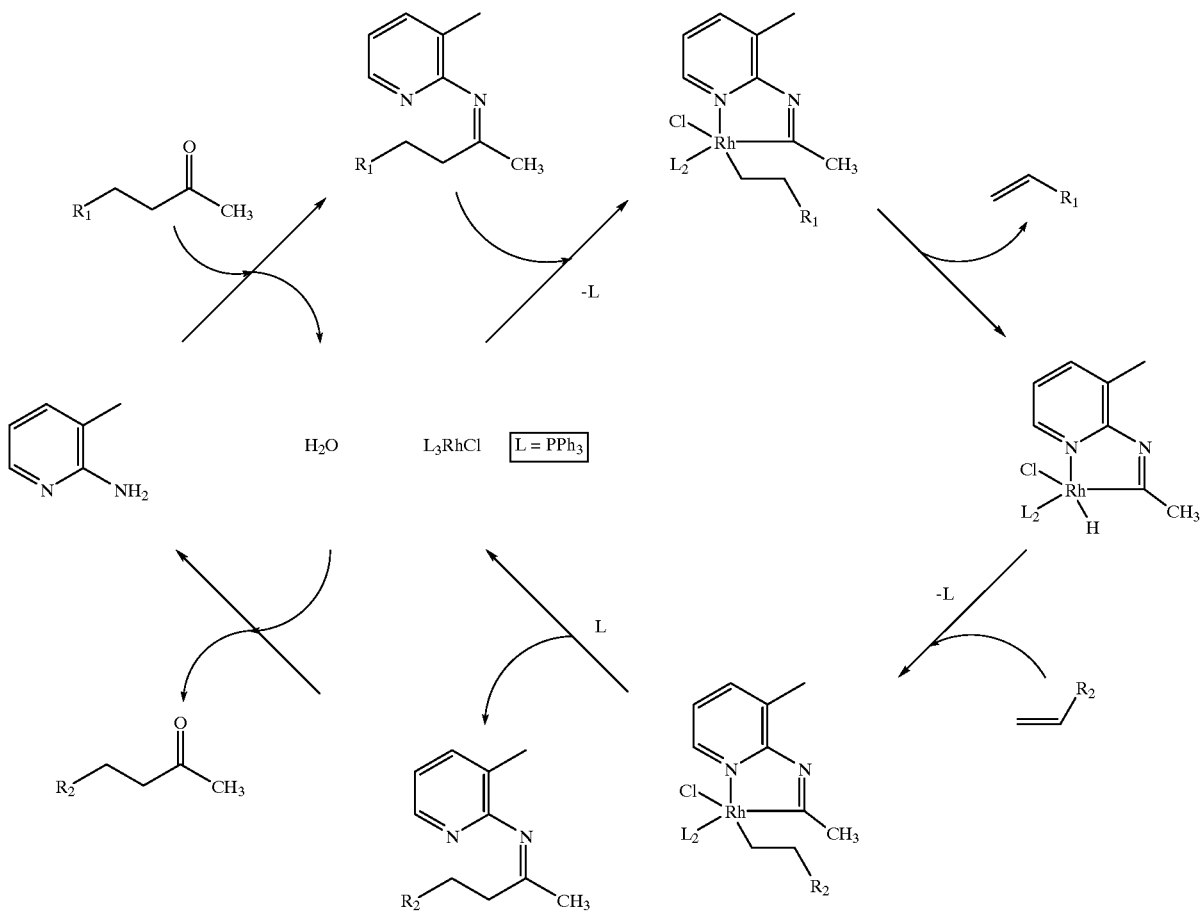

As shown in the chemical reaction formula 2, the reaction starts with the formation of ketimine through the condensation of ketone with 2-amino-3-pycoline. The transition metal catalyst is coordinated to the pyridine radical of the formed ketimine to cleave the carbon-carbon bond, resulting in forming an olefin by β-hydrogen removal. Subsequently, exchanging with the removed olefin, a reactant olefin is newly coordinated to the transition metal to form a new ketimine. This ketimine is hydrolyzed by the water formed in the condensation of the early stage to recover the amine and to produce a new ketone. Herein, the transition metal complex takes part in two reactions: condensation and hydroacylation.

A better understanding of the present invention may be obtained in light of the following examples which are set forth illustrate, but are not to be construed to limit the present invention.

EXAMPLE 1

In a 0.5 ml pressure reactor, amino-3-pycoline 5 mg (0.046 mmol), benzyl acetone 32 mg (0.22 mmol), tristriphenylphosphine rhodium (I) chloride 20 mg (0.022 mmol) (10 mol % based on benzyl acetone), and 1-octene 244 mg (2.18 mmol) were placed and dissolved in toluene 100 mg. While the reactor was stopped with a stopper, the reactants were heated at 150° C. for 48 hours with stirring.

After completion of the reaction, 2-decanone was found to be obtained at a yield of 75% as measured by gas chromatography. The reaction products were separated by column chromatography on silica gel eluting with a mixture of 5:2 hexane:ethyl acetate to obtain colorless oily 2-decanone 25 mg (0.16 mmol). Yield: 75%.

Under the same condition, a variety of olefins were employed, and the results are given in Table 1, below.

TABLE 1

| Olefins | Products | Yield (%) |
| --- | --- | --- |
| 1-Hexene | 2-Octanone | 86 |
| 3,3-Dimethyl-1-butene | 5,5-Dimethyl-2-hexanone | 100 |
| Vinylcyclohexane | 4-Cyclohexyl-2-butanone | 42 |
| Cyclohexene | Cyclohexylmethyl ketone | 55 |
| Cyclopentene | Cyclopentylmethyl ketone | 13 |
| Alkyl benzene | 5-Phenyl-2-pentanone | 27 |
| 1-Pentene | 2-Heptanone | 61 |
| Cyclooctene | Cyclooctylmethyl ketone | 4 |

EXAMPLE 2

In a 0.5 ml pressure reactor, amino-3-pycoline 5 mg (0.046 mmol), benzyl acetone 32 mg 0.22 mmol), tristriphenylphosphine rhodium (I) chloride 20 mg (0.022 mmol) (13 mol % based on benzyl acetone), and 1-hexene 179 mg (2.13 mmol) were placed and dissolved in toluene 100 mg. While the reactor was stopped with a stopper, the reactants were heated at 150° C. for various time periods with stirring.

After completion of the reaction, gas chromatography was conducted to determine the yields of 2-octanone obtained according to the time change and the results are given in Table 2, below.

TABLE 2

| Nos. | Time (hours) | Yield (%) |
|---|---|---|
| 1 | 6 | 20 |
| 2 | 24 | 77 |
| 3 | 48 | 86 |

Under the same reaction procedure and condition as in Example 2 (tristriphenylphosphine rhodium (I) chloride 10 mol %, 2-amino-3-pycoline 20 mol %, 48 hours, toluene 100 mg), benzyl acetone 32 mg (0.22 mmol) and 1-hexene 273 mg (3.24 mmol) were reacted at various temperatures with stirring.

After completion of the reaction, gas chromatography was conducted to determine the yields of 2-octanone obtained according to the temperature change and the results are given in Table 3, below.

TABLE 3

| Nos. | Temp. °C. | Yield (%) |
|---|---|---|
| 1 | 100 | 0.4 |
| 2 | 130 | 19 |
| 3 | 150 | 86 |
| 4 | 180 | 55 |

EXAMPLE 4

Under the same reaction procedure and conditions as in Example 2 (tristriphenylphosphine rhodium (I) chloride 10 mol %, 150° C., 48 hours, toluene 100 mg), benzyl acetone 32 mg (0.22 mmol) and 1-hexene 182 mg (2.16 mmol) were reacted in the presence of various amounts of 2-amino-3-pycoline. A measurement was made of the yields of 2-octanone, and the results are given in Table 4, below. When 2-amino-3-pycoline was absent, 2-octanone was not obtained at all and benzyl acetone was recovered in its entirety.

TABLE 4

| Nos. | Amounts of 2-Amino-3-pycoline (mol % based on Aldehyde) | Yield (%) |
|---|---|---|
| 1 | 0 | 0 |
| 2 | 20 | 86 |
| 3 | 50 | 67 |
| 4 | 100 | 95 |

EXAMPLE 5

Reaction between Benzyl Acetone and 1-Hexene in the Presence of Tristriphenylphosphine Rhodium (I) Chloride Under Various Amines Under the same reaction procedure and conditions as in Example 2 (tristriphenylphosphine rhodium (I) chloride 10 mol %, 150° C., 48 hours), benzyl acetone 32 mg (0.22 mmol) and 1-hexene 182 mg (2.16 mmol) were reacted in toluene 100 mg in the presence of various amines (20 mol % based on benzyl acetone). A measurement was made of the yields of 2-octanone and the results are given in Table 5, below.

TABLE 5

| Nos. | Amine Derivatives | Yield (%) |
|---|---|---|
| 1 | 2-Amino-3-pycoline | 86 |
| 2 | 2-Amino-3-pycoline | 58 |
| 3 | 2-Amino-3-pycoline | 68 |
| 4 | 2-Amino-3-pycoline | 23 |
| 5 | 2-Aminopyridine | 59 |

EXAMPLE 6

Under the same reaction procedure and conditions as in Example 2 (tristriphenylphosphine rhodium (I) chloride 10 mol %, 2-amino-3-pycoline 20 mol %, 150° C., 48 hours), benzyl acetone 32 mg (0.22 mmol) was reacted with various amounts of 1-hexene in toluene 100 mg. A measurement was made of the yields of 2-octanone and the results are given in Table 6, below.

TABLE 6

| Nos. | Amounts of 1-Hexene (mol % based on Benzyl Acetone) | Yield (%) |
|---|---|---|
| 1 | 91 mg (500 mol %) | 49 |
| 2 | 182 mg (1000 mol %) | 86 |
| 3 | 273 mg (1500 mol %) | 98 |

EXAMPLE 7

Under the same reaction procedure and conditions as in Example 2 (2-amino-3-pycoline 20 mol %, 150° C., 48 hours), benzyl acetone 32 mg (0.22 mmol) and 1-hexene 182 mg (2.16 were reacted in toluene 100 mg in the presence of various metal catalysts (10 mol % based on benzyl acetone). A measurement was made of the yields of 2-octanone and the results are given in Table 7, below.

TABLE 7

| Nos. | Metal Catalyst | Yield (%) | Additive |
|---|---|---|---|
| 1 | Rh(CO)(PPh$_3$)$_2$Cl | 12 | |
| 2 | RhCl$_3$·xH$_2$O | 7 | PPh$_3$(5x Cat.) |
| 3 | Ir(PPh$_3$)$_3$Cl | 1 | |
| 4 | [Rh(C$_8$H$_{16}$)Cl]$_2$ | 33 | PPh$_3$(2x Cat.) |
| 5 | [Rh(C$_8$H$_{16}$)Cl]$_2$ | 46 | PPh$_3$(3x Cat.) |
| 6 | [Rh(C$_8$H$_{16}$)Cl]$_2$ | 37 | PPh$_3$(5x Cat.) |
| 7 | [Rh(C$_8$H$_{16}$)Cl]$_2$ | 15 | P(C$_6$H$_4$(CH$_3$))$_3$(2x Cat.) |
| 8 | [Rh(C$_8$H$_{16}$)Cl]$_2$ | 6 | P(C$_6$H$_{11}$)$_3$(2x Cat.) |
| 9 | [Rh(C$_8$H$_{16}$)Cl]$_2$ | 18 | P(C$_6$H$_{11}$)$_2$Ph(2x Cat.) |
| 10 | [Rh(C$_8$H$_{16}$)Cl]$_2$ | 7 | P(C$_6$H$_4$(OCH$_3$))$_3$(2x Cat.) |
| 11 | [Rh(C$_8$H$_{16}$)Cl]$_2$ | 6 | Ph$_2$PCH$_2$CH$_2$PPh$_2$(5x Cat.) |

EXAMPLE 8

Under the same reaction procedure and conditions as in Example 2 (tristriphenylphosphine rhodium (I) chloride 10 mol %, 2-amino-3-pycoline 20 mol %, 150° C., 48 hours, benzyl acetone 32 mg (0.22 mmol) and 1-hexene 273 mg (3.24 mmol) were reacted in various amounts of toluene.

After completion of the reaction, gas chromatography was conducted to determine the yields of 2-octanone obtained according to the charge in the amount of toluene and the results are given in Table 8, below.

TABLE 8

| Nos. | Toluene (mg) | Yield (%) |
| --- | --- | --- |
| 1 | 0 | 74 |
| 2 | 50 | 72 |
| 3 | 100 | 98 |
| 4 | 200 | 56 |

EXAMPLE 9

In a 0.5 ml pressure reactor, amino-3-pycoline 23 mg (0.21 mmol), benzyl acetone 32 mg (0.22 mmol), tristriphenylphosphine rhodium (I) chloride 20.0 mg (0.022 mmol) (10 mol % based on benzyl acetone), and 1-octene 263 mg 2.34 mmol) were placed and dissolved in toluene 100 mg. While the reactor was stopped with a stopper, the reactants were heated at 150° C. for 48 hours with stirring.

After completion of the reaction, 2-decanone was found to be obtained at a yield of 96% as measured by gas chromatography. The reaction products were separated by column chromatography on silica gel eluting with a mixture of 5:2 hexane:ethyl acetate to obtain colorless oily 2-decanone 25 mg (0.16 mmol). Yield: 89%.

Under the same conditions, a variety of olefins (3.24 mmol) were employed, and the results are given in Table 9, below.

TABLE 9

| Olefins | Products | Yield (%) |
| --- | --- | --- |
| 1-Hexene | 2-Octanone | 96 |
| 3,3-Dimethyl-1-butene | 5,5-Dimethyl-2-hexanone | 100 |
| Vinylcyclohexane | 4-Cyclohexyl-2-butanone | 55 |
| Cyclohexene | Cyclohexylmethyl ketone | 92 |
| Cyclopentene | Cyclopentylmethyl ketone | 30 |
| Alkyl benzene | 5-Phenyl-2-pentanone | 37 |
| 1-Pentene | 2-Heptanon | 92 |

EXAMPLE 10

In a 0.5 ml pressure reactor, amino-3-pycoline 5 mg 0.046 mmol), 1,4-diphenyl-1-propanone 46 mg (0.22 mmol), tristriphenylphosphine rhodium (I) chloride 22.0 mg (0.024 mmol) (10 mol % based on 1,4-diphenyl-1-propanone), and 1-hexene 189 mg (2.25 mmol) were placed and dissolved in toluene 100 mg. While the reactor was stopped with a stopper, the reactants were heated at 150° C. for 48 hours with stirring.

After completion of the reaction, heptanophenone was found to be obtained at a yield of 58% as measured by gas chromatography. The reaction products were separated by column chromatography on silica gel eluting with a mixture of 5:2 hexane:ethyl acetate to obtain colorless oily heptanophenone 23 mg (0.12 mmol). Yield: 55%

Under the same conditions, a variety of ketones were employed, and the results are given in Table 10, below.

TABLE 10

| Aldehyde | Products | Yield (%) | Note |
| --- | --- | --- | --- |
| 2-Butanone | 2-Octanone | 61 | |
| 2-Octanone | 2-Decanone | 77 | 1-Octene instead of 1-hexene |
| 1,5-Diphenyl-3-pentanone | 7-Tridecanone, 1-Phenyl-3-nonanone | 19, 32 | |
| 2,6-Dimethyl-4-heptanone | 7-Tridecanone, 2-Methyl-4-decanone | 6, 7 | |

EXAMPLE 11

In a 0.5 ml pressure reactor, N-(3-methyl-2-pyridyl)-N-(phenetylethylidene)amine (a ketimine resulting from the condensation of benzyl acetone and 2-amino-3-pycoline) 52.6 mg (0.221 mmol), tristriphenylphosphine rhodium (I) chloride 9.9 mg (0.011 mmol) (5 mol % based on the ketimine), and hexene 182.3 mg (2.17 mmol) were placed and dissolved in toluene 94.8 mg. While the reactor was stopped with a stopper, the reactants were heated at 150° C. for 6 hours with stirring. After completion of the reaction, N-(1-methylheptylidene)-N-(3-methyl-2-pyridinyl)amine was found to be obtained at a yield of 82% as measured by gas chromatography.

The same procedure was repeated except that, instead of tristriphenylphosphine rhodium (I) chloride, [Rh($C_8H_{16}$)Cl]$_2$ 4.1 mg (0.011 mmol) (5 mmol based on the ketimine) and P($C_8H_{11}$)$_3$ 8.4 mg (0.03 mmol) (three times as much as the catalyst) were used. After completion of the reaction, N-(1-methylheptylidene)-N-(3-methyl-2-pyridinyl) amine was found to be obtained at a yield of 76% as measured by gas chromatography. The ketimine could be converted into a ketone by hydrolysis.

In contrast to conventional preparation methods of ketone which employ multi-stage reactions or aldehyde or alcohol as a starting material, suffering from high production cost and low yield, the present invention, as described hereinbefore, allows the synthesis of high-value ketone from low-value ketone at high yields. In addition, the present invention is very advantageous in that it can be applied to all of the ketones which contain the β-hydrogen relative to the carbonyl group.

The present invention has been described in an illustrative manner, and is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A method for preparing a ketone, comprising the steps of:

preparing a reactant mixture comprising a ketone containing β-hydrogen relative to the carbonyl group and a vinyl olefin or internal olefin having an aliphatic or aromatic alkyl moiety as starting materials; and reacting the reactant mixture at approximately 100–180° C. for at least 6 hours in the presence of a rhodium or iridium transition metal catalyst and a 2-aminopyridine derivative.

2. The method as set forth in claim 1, wherein the rhodium transition metal catalyst is selected from the group consisting of rhodium monovalent compounds, phosphine-added rhodium monovalent compounds, rhodium trivalent compounds and phosphine-added rhodium trivalent compounds.

3. The method as set forth in claim 1, wherein the 2-aminopyridine derivative is 2-amino-3-pycoline.

4. A method for preparing a ketone, comprising the steps of:

producing a ketimine through the condensation of a reactant ketone and 2-amino-3-pycoline;

coordinating a transition metal catalyst to the pyridine radical of the ketimine to cleave a carbon-carbon bond of the reactant ketone and to subsequently remove a β-hydrogen to form an olefin;

coordinating a substitute, different olefin to the metal of the catalyst to produce a different ketimine; and hydrolyzing the different ketimine with the water resulting from the condensation to recover the amine.

* * * * *